(12) United States Patent
Noh

(10) Patent No.: US 11,596,154 B2
(45) Date of Patent: Mar. 7, 2023

(54) HEALTH FUNCTIONAL FOOD PRODUCT PREPARED BY FERMENTING A DOUGH CONTAINING WHEY

(71) Applicant: Han Seung Noh, Gwangju (KR)

(72) Inventor: Han Seung Noh, Gwangju (KR)

(*) Notice: Subject to any disclaimer, the term of this patent is extended or adjusted under 35 U.S.C. 154(b) by 583 days.

(21) Appl. No.: 16/609,970

(22) PCT Filed: Jul. 29, 2019

(86) PCT No.: PCT/KR2019/009378
§ 371 (c)(1),
(2) Date: Oct. 31, 2019

(87) PCT Pub. No.: WO2021/006409
PCT Pub. Date: Jan. 14, 2021

(65) Prior Publication Data
US 2021/0360938 A1    Nov. 25, 2021

(30) Foreign Application Priority Data
Jul. 11, 2019  (KR) .................. 10-2019-0083753

(51) Int. Cl.
| A21D 2/26 | (2006.01) |
| A23L 33/19 | (2016.01) |
| A23L 33/14 | (2016.01) |
| A23L 33/135 | (2016.01) |
| A21D 8/04 | (2006.01) |
| A23L 3/3463 | (2006.01) |

(52) U.S. Cl.
CPC .......... *A21D 2/263* (2013.01); *A21D 8/045* (2013.01); *A21D 8/047* (2013.01); *A23L 3/3463* (2013.01); *A23L 33/135* (2016.08); *A23L 33/14* (2016.08); *A23L 33/19* (2016.08); *A23Y 2220/00* (2013.01); *A23Y 2260/00* (2013.01)

(58) Field of Classification Search
None
See application file for complete search history.

(56) References Cited

U.S. PATENT DOCUMENTS

| 6,066,343 A | * | 5/2000 | Megeed | ................ A21D 8/045 |
| | | | | 426/549 |
| 2016/0192689 A1 | * | 7/2016 | Horn | .................. A23L 33/22 |
| | | | | 424/93.46 |
| 2017/0130251 A1 | * | 5/2017 | Brady | ................. C12N 15/815 |

FOREIGN PATENT DOCUMENTS

| CN | 1695492 | * 11/2005 | ............... A23L 1/29 |
| KR | 10-0923051 B1 | 10/2009 | |
| KR | 10-1884634 B1 | 8/2018 | |

* cited by examiner

*Primary Examiner* — Felicia C Turner
(74) *Attorney, Agent, or Firm* — MH2 Technology Law Group, LLP

(57) ABSTRACT

A health functional food product prepared by fermenting a dough containing whey, including a health functional bakery product prepared by: preparing a sponge and a dough by adding and mixing about 1.0 to 10 wt part of a whey powder and about 0.01 to 1.0 wt part of a mixture of probiotic preparation consisting of *Leuconostoc* strain, *Lactobacillus* strain and 2 kinds of *Saccharomyces* strains as to 100 wt part of a dough; and fermenting, aging and baking the dough. Such may be used to prepare a health functional bakery product as well as a health functional *Lactobacillus* fermented drink using said health functional bakery product.

1 Claim, 1 Drawing Sheet

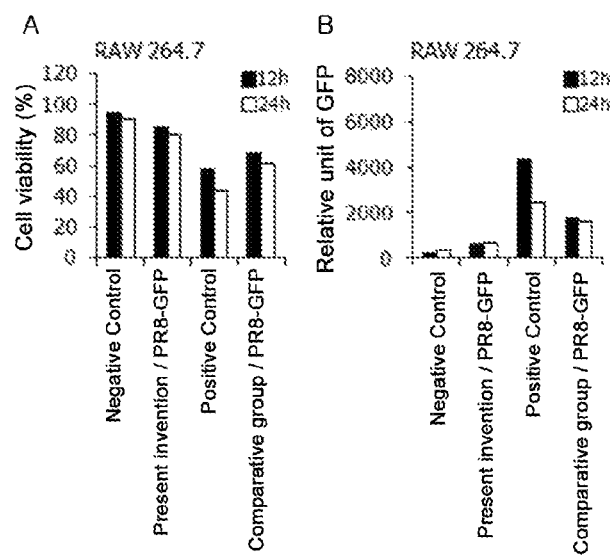

HEALTH FUNCTIONAL FOOD PRODUCT PREPARED BY FERMENTING A DOUGH CONTAINING WHEY

CROSS-REFERENCE TO RELATED APPLICATIONS

This application is the U.S. National Phase Application for International Application Number PCT/KR2019/009378, filed on 29 Jul. 2019, which claims priority to Korean Application No. 10-2019-0083753 filed on 11 Jul. 2019, the entire disclosures of which are hereby incorporated by reference in their entirety.

TECHNICAL FIELD

The present invention relates to a health functional food product prepared by fermenting a dough containing whey. More specifically, the present invention relates to a health functional bakery product prepared by the steps comprising: preparing a sponge and a dough by adding and mixing 1.0 to 10 wt part of a whey powder and 0.01 to 1.0 wt part of a mixture of probiotic preparation consisting of Leuconostoc sp. strain, Lactobacillus sp. strain and 2 kinds of Saccharomyces sp. strains as to 100 wt part of a dough; and fermenting, aging and baking the dough to prepare a health functional bakery product as well as a health functional Lactobacillus fermented drink using said health functional bakery product.

DESCRIPTION OF PRIOR ART

Modern people have been enduring the homeostasis disturbance of human body due to dietary change to high calorie meals, lack of exercise and increase of stress. Accordingly, various kinds of obesity and related metabolic disease have been increasing rapidly. Abdominal obesity in middle aged person can be a direct cause of chronic metabolic syndrome. Especially, in abdominal obesity, the fat can be easily dissolved and absorbed into the blood, which can result in the metabolic syndrome.

The World Health Organization (WHO) has classified the obesity as a disease in 1996 and specified it as an object to be prevented or treated. Recently, preparations for treating or preventing obesity have been developed using probiotics, which contains a live strain of Bifidobacteria.

In Korean Patent No. 10-923051 "Functional live strain preparation and a bread prepared using the same", the inventor of present invention has disclosed a functional live strain preparation mixing Leuconostoc strain and Saccharomyces yeast strain for increasing the production of oligo sugar at the time of starch fermentation.

Also, In Korean Patent No. 10-1884634 "Lactobacillus fermented drink having weight control effect", the inventor of present invention has disclosed a Lactobacillus fermented drink having weight control effect prepared by producing a bread using functional live strain preparation as described in inventor's previous patent disclosure; and fermenting and aging said bread using Lactobacillus sp. nhs221 strain culture for making a Lactobacillus fermented drink.

Whey is a liquid substance remaining from the milk in the course of preparing a cheese from milk. Usually, the whey contains 3-5 wt % of lactose, less than 1 wt % of whey protein and traceable amount of fat and ash. Whey protein has been known to contain a large amount of amino acid ingredients that enables the optimal synthesis of the muscle in the human body. It has been believed that ingesting such whey protein before and after exercise will help the human body to be diet and effective for blood glucose control in parallel with exercise.

For the application of health function of whey, the inventor of present invention has developed a health functional bread using whey modifying the preparation method disclosed in inventor's own previous patent of Korean Patent No. 10-923051 with the steps comprising: preparing a sponge and a dough by adding and mixing 1.0 to 10 wt part of a whey powder and 0.01 to 1.0 wt part of a mixture of probiotic preparation consisting of Leuconostoc sp. strain, Lactobacillus sp. strain and 2 kinds of Saccharomyces sp. strains as to 100 wt part of a dough; and fermenting, aging and baking the dough to prepare a health functional bakery product.

Finally, the present invention has been completed by confirming the health functions of the blood sugar controlling effect, the anti-bacterial effect and/or the viral disease preventing effect of bakery product and Lactobacillus fermented drink of the present invention.

Problem to be Solved

The problem to be solved is to develop a health functional bakery product prepared by the steps comprising: preparing a sponge and a dough by adding and mixing 1.0 to 10 wt part of a whey powder and 0.01 to 1.0 wt part of a mixture of probiotic preparation consisting of Leuconostoc sp. strain, Lactobacillus sp. strain and 2 kinds of Saccharomyces strains sp. as to 100 wt part of a dough; and fermenting, aging and baking the dough to prepare a health functional bakery product as well as a health functional Lactobacillus fermented drink using said health functional bakery product having the blood sugar controlling effect, the anti-bacterial effect and/or the viral disease preventing effect.

Means for Solving the Problem

The object of the present invention is to provide a process for preparing a health functional food product comprising the steps of: 1) preparing a sponge and a dough by adding and mixing 1.0 to 10 wt part of a whey powder as to 100 wt part of a dough; and 2) baking the dough for preparing a health functional bakery product after adding, mixing and fermenting 0.01 to 1.0 wt part of a mixture of probiotic preparation consisting of Leuconostoc sp. strain, Lactobacillus sp. strain and 2 kinds of Saccharomyces sp. strains, wherein said mixture of probiotic preparation consists of Leuconostoc sp. nhs210 strain (accession No.: KCTC-11226BP), Lactobacillus sp. nhs221 strain (accession No.: KCTC-11749BP), Saccharomyces sp. CCRG321 strain (accession No.: KCTC-13300BP) and Saccharomyces sp. nhs321 strain (accession No.: KCTC-11227BP).

The another object of the present invention is to provide a health functional food product comprising the steps of: 1) Adjusting a sugar content into 10~15° Brix after adding and mixing 300-500 wt part of purified water, 0.1~10 wt part of whey powder and small amount of sucrose and/or fructose as to 100 wt part of dried and crushed health functional bakery product containing a mixture of probiotic preparation prepared by above process; 2) fermenting and aging the mixture prepared in step 1) for 40 to 70 days in room temperature after adding and mixing 0.5 to 2.0 wt part (1.0~8.0×10⁸ CFU) of Lactobacillus sp. strain (accession No.: KCTC-11749BP) cultivation preparation; and 3) obtaining a health functional Lactobacillus fermented drink, wherein said mixture of probiotic preparation consists of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP).

Further, said *Saccharomyces* sp. CCRG321 strain (accession No.: KCTC-13300BP) is isolated and obtained by the steps comprising: 1) spreading PDA (Potato dextrose agar) separation medium containing 3 wt % whey powder in the flat plate; 2) inoculating and culturing a wild type bread yeast as parent strain; and 3) isolating a fast and optimally growing yeast strain with 3 times subculturing.

The further object of the present invention is to provide a health functional bakery product, wherein the blood sugar controlling effect can be measured in vivo in a diabetic mouse animal model.

The further object of the present invention is to provide a health functional bakery product, wherein the anti-bacterial effect can be measured in vitro against *Salmonella enterica*, *Escherichia coli* and/or *Staphylococcus aureus*.

The further object of the present invention is to provide a health functional *Lactobacillus* fermented drink, wherein the viral disease preventing effect can be measured in vitro against influenza virus.

Advantageous Effect

The advantageous effect of present invention is to provide a health functional bakery product prepared by the steps comprising: preparing a sponge and a dough by adding and mixing 1.0 to 10 wt part of a whey powder and 0.01 to 1.0 wt part of a mixture of probiotic preparation consisting of *Leuconostoc* sp. strain, *Lactobacillus* sp. sp. strain and 2 kinds of *Saccharomyces* sp. strains as to 100 wt part of a dough; and fermenting, aging and baking the dough to prepare a health functional bakery product as well as a health functional *Lactobacillus* fermented drink using said health functional bakery product having the blood sugar controlling effect, the anti-bacterial effect and/or the viral disease preventing effect.

BRIEF DESCRIPTION OF DRAWINGS

FIG. 1 is a graph showing the results of antiviral activity experiment using PR8-GFP (influenza virus-green fluorescent protein) regarding the *Lactobacillus* fermented drink prepared in Preparation Example 2 of the present invention. FIG. 1A shows the cell viability of RAW 264.7 and FIG. 1B shows the GFP (green fluorescence protein) relative absorption unit.

PREFERRED EMBODIMENT OF INVENTION

The present invention relates to a process for preparing a health functional food product comprising the steps of: 1) preparing a sponge and a dough by adding and mixing 1.0 to 10 wt part of a whey powder as to 100 wt part of a dough; and 2) baking the dough for preparing a health functional bakery product after adding, mixing and fermenting 0.01 to 1.0 wt part of a mixture of probiotic preparation consisting of *Leuconostoc* sp. strain, *Lactobacillus* sp. strain and 2 kinds of *Saccharomyces* sp. strains, wherein said mixture of probiotic preparation consists of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP).

Further, the present invention also relates to a health functional food product comprising the steps of: 1) Adjusting a sugar content into 10~15° Brix after adding and mixing 300-500 wt part of purified water, 0.1~10 wt part of whey powder and small amount of sucrose and/or fructose as to 100 wt part of dried and crushed health functional bakery product containing a mixture of probiotic preparation prepared by above process; 2) fermenting and aging the mixture prepared in step 1) for 40 to 70 days in room temperature after adding and mixing 0.5 to 2.0 wt part ($1.0~8.0 \times 10^8$ CFU) of *Lactobacillus* sp. strain (accession No.: KCTC-11749BP) cultivation preparation; and 3) obtaining a health functional *Lactobacillus* fermented drink, wherein said mixture of probiotic preparation consists of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP).

The present invention can be explained more precisely as follows.

The mixture of probiotic preparation for fermenting and aging a health functional bakery product of the present invention is a mixture of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP).

Further, said *Saccharomyces* sp. CCRG321 strain (accession No.: KCTC-13300BP) isolated from a wild type baker's yeast as parent strain shall be included for fermenting a dough having a whey powder.

Further, said *Saccharomyces* sp. CCRG321 strain (accession No.: KCTC-13300BP) can be isolated and obtained by the steps comprising: spreading PDA (Potato dextrose agar) separation medium containing 3 wt % whey powder in the flat plate; inoculating and culturing a wild type baker's yeast as parent strain; and isolating a fast and optimally growing yeast strain with 3 times subculturing.

Further, the whey powder has been prepared by concentrating and spray drying the whey remained after manufacturing the cheese, wherein the whey powder contains 18 wt % of whey protein, 18 wt % of carbohydrate, 18 wt % of crude lipid and 18 wt % of water.

The inventor of present invention has tried to isolate and obtain a fast and optimally growing yeast strain in the medium containing whey powder with following steps comprising; spreading PDA (Potato dextrose agar) separation medium containing 3 wt % whey powder in the flat plate; inoculating and culturing a wild type baker's yeast as parent strain; and isolating fast and optimally growing yeast strain with 3 times subculturing. Finally, the isolated strain has been named as *Saccharomyces* sp. CCRG321 strain. Further, this novel isolated strain has been internationally deposited as accession No.: KCTC-13300BP under Budapest Treaty on Jul. 18, 2017 with Korean Collection for Type Cultures.

The morphological characteristics of the novel strain *Saccharomyces* sp. CCRG321 yeast strain (accession number: KCTC-13300BP) of the present invention have been generally common with the *Saccharomyces cerevisiae* baker's yeast strain. Unlike conventional strains of *Saccharomyces* genus, however, it has been turned out to be a novel optimally growing strain, while releasing a large amount of carbon dioxide gas in PDA medium containing whey powder.

To confirm this characteristics, the 1×103 CFU/ml amount of isolated yeast strain of the present invention has been inoculated into 100 wt part PDA medium containing 3 wt part of whey powder. Then, the amount of generated carbon dioxide has been measured at 24 hours and at 36 hours respectively. As a control group, the bakery commercial yeast sold by Jenico Ltd. has been used. Table 1 shows the amount of generated carbon dioxide.

TABLE 1

|  | Amount of Carbon Dioxide (ml) | |
| --- | --- | --- |
|  | 24 hrs | 36 hrs |
| Yeast strain of present invention (KCTC-13300BP) | 6 | 14 |
| Jenico's yeast | 3 | 9 |

In order to measure the assimilative activity of the *Saccharomyces* sp. CCRG321 strain (accession number: KCTC-13300BP) of the present invention, 20 g/L of fructose, 20 g/L of glucose or 20 g/L of whey powder have been added to YPD basic liquid medium (yeast extract 1%, bactopeptone 1%, glucose 2%) respectively. Then, the assimilation of each fructose, glucose and whey powder has been measured.

After 0 hours, 12 hours, 24 hours and 36 hours from yeast strain inoculation, the broth of *Saccharomyces* sp. CCRG321 yeast strain (accession No.: KCTC-13300BP) grown in a YPD liquid medium supplemented with fructose, glucose or whey powder has been collected. Then, the collected broth has been centrifuged, washed and measured with spectrophotometer. Table 2 shows the dried cell mass after culturing the yeast strain of the present invention.

TABLE 2

|  | 0 hr | 12 hrs | 24 hrs | 36 hrs |
| --- | --- | --- | --- | --- |
| fructose | 0.05 | 2.0 | 3.3 | 4.6 |
| glucose | 0.05 | 1.8 | 3.2 | 4.5 |
| whey poweder | 0.05 | 1.4 | 3.8 | 5.1 |

(unit: g/L)

As shown in Table 2, the whey powder assimilation of the *Saccharomyces* sp. CCRG321 yeast strain of the present invention (accession number: KCTC-13300BP) has been lower than that of fructose or glucose after 12 hours of incubation, However, whey powder showed higher assimilation than that of fructose or glucose. after 24 hours of incubation, Using the *Saccharomyces cerevisiae* sp. CCRG321 yeast strain (accession number: KCTC-13300BP) of the present invention, it has been confirmed that the dough containing the whey powder can be manufactured into a health functional bakery product when fermented at low temperature for more than 24 hours.

Further, a health functional bakery product of the present invention can be explained based upon the probiotic preparation consisting of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP).

The health functional bakery product of the present invention can be applied into various kinds of food product. As a representative example of food product, a health functional *Lactobacillus* fermented drink can be applied.

Hereinafter, a method for producing a health functional *Lactobacillus* fermented drink according to the present invention will be described.

(Step 1) A sponge and a dough is prepared by adding and mixing 1.0 to 10 wt part of a whey powder as to 100 wt part of a dough.

(Step 2) A health functional bakery product is prepared by baking the dough prepared in step 1 after adding, mixing and fermenting 0.01 to 1.0 wt part of a mixture of probiotic preparation consisting of *Leuconostoc* sp. strain, *Lactobacillus* sp. strain and 2 kinds of *Saccharomyces* sp. strains. Further, said mixture of probiotic preparation consists of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP).

(Step 3) A sugar content is adjusted into 10~15° Brix, after adding and mixing 300-500 wt part of purified water, 0.1~10 wt part of whey powder and small amount of sucrose and/or fructose as to 100 wt part of dried and crushed health functional bakery product prepared in step 2.

(Step 4) A health functional *Lactobacillus* fermented drink is obtained after fermenting and aging the mixture prepared in step 3 for 40-70 days in room temperature after adding and mixing 0.5 to 2.0 wt part (1.0~8.0×108 CFU) of *Lactobacillus* sp. strain (accession No.: KCTC-11749BP) cultivation preparation.

The present invention can be explained in detail by following Preparation Examples, Comparative Preparation Examples and Examples.

(Raw Material 1) Isolation of *Leuconostoc* sp. nhs210 strain (accession No.: KCTC-11226BP) and *Saccharomyces* sp. nhs321 strain (accession No.: KCTC-11227BP)

The isolation method of *Leuconostoc* sp. nhs210 strain (accession No.: KCTC-11226BP) and *Saccharomyces* sp. nhs321 strain (accession No.: KCTC-11227BP) has been disclosed in inventor's own prior Korean Patent No. 10-923, 051 "Health functional probiotic preparation and Bread using the same".

(Raw Material 2) Isolation of *Lactobacillus* sp. nhs221 (accession No.: KCTC-11749BP)

After adding the natural fruit juice to the sponge for preparing a bread, the sponge has been allowed to stand at room temperature for 1 week, in order to contact with microorganisms for culture. After drying the cultured sponge, microorganisms have been further grown for 2-3 days under anaerobic conditions at room temperature. The 10 pieces (5 mg per piece) of dried sponges collected from 10 places containing the microorganisms has been dispensed into 10 cultured dishes. Microorganisms have been cultured in culture dishes containing 5 g of starch per culture medium for 48 hours at 20° C. in 75% humidity. Among 10 culture dishes, only one culture dish where *Lactobacillus* is produced in the most has been selected for subculture. Finally, only *Lactobacillus* sp. strain has been isolated and identified in the mixture of yeast strains and *Lactobacillus* sp. strain.

(Raw Material 3) Isolation of *Saccharomyces* sp. CCRG321 (accession No.: KCTC-13300BP)

*Saccharomyces* sp. CCRG321 strain has been isolated and obtained by following steps. PDA (Potato dextrose agar) separation medium containing 3 wt % whey powder has been spread in the flat plate. a wild type baker's yeast as parent strain has been inoculated and cultured. Finally, a fast and optimally growing yeast strain after 3 times subculture has been isolated and identified.

(Preparation Example 1) Preparation of Health Functional Bread of the Present Invention A sponge and a dough has been prepared by adding and mixing 30 g of whey powder as to 1000 g of dough containing flour, milk, eggs, butter, sugar, salt and water. Further, 2 g of probiotic preparation consisting of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP) has been added and mixed to the dough. After fermenting and aging the dough at low temperature twice, the fermented dough has been baked in oven at 180° C. Finally, the health functional bread of the present invention has been prepared.

(Preparation Example 2) Preparation of Health Functional *Lactobacillus* Drink of the Present Invention The health functional bread prepared in Preparation Example 1 has been dried and crushed. The sugar content has been adjusted into 10 to 15° Brix after adding and mixing 300-500 ml of purified water, 2 g of whey powder and small amount of sucrose and/or fructose as to 100 g of health functional bread. After adding and mixing 1.0 ml (1.0~8.0×10⁸ CFU) of *Lactobacillus* sp. strain (accession No.: KCTC-11749BP) cultivation preparation, the mixture has been fermented and aged for 50 days at room temperature. Finally, the health functional *Lactobacillus* fermented drink of the present invention has been prepared.

(Comparative Preparation Example 1) Preparation of Conventional Bread (without Adding Probiotic Preparation and Whey)

The conventional bread has been prepared as the same manner of Preparation Example 1, except that Jenico's yeast has been replaced by probiotic preparation consisting of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP) and whey powder has not been added to the dough.

(Comparative Preparation Example 2) Preparation of *Lactobacillus* Fermented Drink (without Adding Probiotic Preparation and Whey)

The *Lactobacillus* fermented drink has been prepared as the same manner of Preparation Example 2, except that Jenico's yeast has been replaced by probiotic preparation consisting of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP) and whey powder has not been added to the dough.

(Example 1) Test for Controlling Blood Glucose in Mouse Test Model 1-1 Test Animal and Induction of Hyperglycemia After feeding a regular diet for one week to ICR male mice having an average weight of 40 g, Streptozotocin (STZ, Sigma, USA, 65 mg/kg BW) dissolved in 0.1 M citrate buffer (pH 4.5) was injected intraperitoneally. After lapse of one week, blood was collected from the tail vein of the mouse at the time of fasting. The blood glucose measured by the simple glucose meter (Glucotrend, Germany) is 300 mg/dL or more. Diabetic mice induced hyperglycemia were used as test animals indicating blood glucose level measured by the simple glucose meter (Glucotrend, Germany) to be 300 mg/dL or more 1-2. Oral Administration of Samples and Blood Glucose Measurement Test animals were divided into streptozotocin-induced diabetic mice divided into Test group (n=10) and Control group (n=10). In Test group, the health functional bread of the present invention prepared in Preparation Example 1 was dissolved in distilled water at an amount of 2 g/Kg mouse, In Control group, the bread prepared in Comparative Preparation Example 1 was dissolved in distilled water at the same dose. Blood was drawn from the tail vein at 0, 30, 60, and 120 minutes after ingestion. Blood glucose level was measured with a simple blood glucose meter (glucotrend, Germeny).

1-3. Measurement of Increasing Amount of Blood Glucose

The blood glucose level at each point was compared with the initial blood glucose level for calculating the blood glucose increase curve. After obtaining the blood glucose increase curve, the area under the curve (AUC) was measured. The blood glucose levels both Test group and Control group was observed at 30, 60 and 120 minutes after oral administration. In Test group, the measured blood glucose levels were 26.3±4.6, 32.2±4.9, and 17.8±3.5 mg/dL, respectively. On the other hand, in Control group, the measured blood glucose levels were 28.3±3.2, 42.8±13.4 and 23.0±6.4 mg/dL, respectively. Therefore, the blood glucose level of Test group were significantly lower than that of Control group.

In Table 3, the increase of blood glucose level (AUC) is shown regarding Test group and Control group after 120 minutes of oral administration of the test samples.

TABLE 3

| | Increase of blood glucose level (AUC)(mg · min/dL) |
|---|---|
| Test group | 910 ± 120.5 |
| Control group | 1132 ± 272.5 |

Test group feeding the bread of the present invention shows the blood glucose controlling effect in an ratio of 19% or more compared to that of Control group. In Test group, the mouse blood glucose increase area for 120 minutes after feeding was 910±120.5 mg·min/dL. On the other hand, in Control group, the mouse blood glucose increase area for 120 minutes after feeding was 1132±272.5 mg·min/dL As a result, the bread prepared by fermenting the dough including the probiotic preparation and whey of the present invention was measured to have a significant blood glucose controlling effect.

(Example 2) Anti-Bacterial Test (Well Diffusion Essay)

Health functional bread dispersion samples (bread content: 1 wt %, 3 wt %) were prepared by dissolving the health functional bread prepared in Preparation Example 1 with water. The live colonies of *Salmonella enterica, E. coli* and *Staphylococcus aureus* were prepared. As a control, the bread dispersion sample (bread content: 1 wt %) was prepared by dissolving bread excluding whey powder and probiotic preparation prepared in Comparative Preparation Example 1 with water.

After placing 30 mg of sterilized Luria-Bertani agar in a sterile Petri plate, 1×107 CFU of *Salmonella enterica, E. coli* and *Staphylococcus aureus* bacteria were added to each petri dish. 100 μl of the health functional bread dispersion sample prepared in Preparation Example 1 was diffused by concentration level (bread content: 1 wt %, 3 wt %). After incubation at 30° C. for 24 hours, the presence and the size of the inhibitory rings were measured.

After diffusing 100 μl of the health functional bread dispersion samples, the size of inhibitory rings (unit: mm) were measured after incubation for 24 hours. The results were shown in Table 4.

TABLE 4

| Sample | *Salmonella enterica,* | *E. coli* | *Staphylococcus aureus* |
| --- | --- | --- | --- |
| bread dispersion 1 wt % | 12 | 10 | 8 |
| bread dispersion 3 wt % | 18 | 16 | 14 |
| Control | No inhibitory ring | No inhibitory ring | No inhibitory ring |

In control, the bread dispersion sample (bread content: 1 wt %) prepared by dissolving bread excluding whey powder and probiotic preparation in Comparative Preparation Example 1 with water could not measure anti-bacterial activity due to the absence of inhibitory ring.

It was confirmed that the anti-bacterial activity of health functional bread dispersion increases in a concentration dependent manner, because the size of inhibitory ring of the health functional bread dispersion sample (bread content: 3 wt %) was larger than that of health functional bread dispersion sample (bread content: 1 wt %).

(Example 3) Anti-Viral Test (Experimental Group)

1 ml of *Lactobacillus* fermented drink prepared in Preparation Example 2 of the present invention was mixed with 1 ml of physiological saline (PBS). Then, 0.1 ml of *Lactobacillus* fermented drink sample was diffused to mouse macrophage cell line RAW 264.7. Finally, virus were inoculated.

Comparative Experimental Group 1 ml of *Lactobacillus* fermented drink prepared in Comparative Preparation Example 2 of the present invention was mixed with 1 ml of physiological saline (PBS). Then, 0.1 ml of *Lactobacillus* fermented drink sample was diffused to mouse macrophage cell line RAW 264.7. Finally, virus were inoculated.

(Negative Control)

Only 0.1 ml of physiological saline (PBS) was diffused to mouse macrophage cell line RAW 264.7. Virus were not inoculated.

(Positive Control)

Only 0.1 ml of physiological saline (PBS) was diffused to mouse macrophage cell line RAW 264.7. Virus were inoculated.

The anti-viral activity of *Lactobacillus* fermented drink of the present invention was carried out against influenza virus as follows.

RAW 264.7 mouse macrophage cell line was cultured in DMEM supplemented with 10% (v/v) of FBS on 6-well TC plate at a concentration of 1×106 cells/well. In Experimental Group, *Lactobacillus* fermented drink sample prepared in Preparation Example 2 was diffused. In Comparative Experimental Group, *Lactobacillus* fermented drink sample prepared in Comparative Preparation Example 2 was diffused. On the other hand, physiological saline (PBS) was diffused in Negative and Positive Control.

Then, the concentration of Experimental Group was adjusted to 50 μg/ml. After 12 hours of treatment, influenza virus PR8-GFP (MOI: 1) were inoculated into RAW 264.7 cells in Experimental Group, Comparative Experimental Group and Positive Control. After 2 hours of inoculation, RAW 264.7 cells were washed with PBS 3 times. After 12-24 hours of replacement with fresh DMEM supplemented with 10% FBS, the degree of virus infection was observed and measured under a microscope using an ultraviolet (345 nm) filter.

FIG. 1B shows data on the amount of GFP expression measured against influenza virus (PR8). In Negative Control, only 0.1 ml of physiological saline (PBS) was diffused into mouse macrophage line RAW 264.7 and the virus was not inoculated. In Positive Control, only 0.1 ml of physiological saline (PBS) was diffused into mouse macrophage line RAW 264.7 and then inoculated with virus.

As shown in FIG. 1B, the PR8-GFP relative units of Experimental Group of the present invention were significantly lower than the PR8-GFP relative units of Comparative Experimental Group.

The RAW 264.7 cell viability in the viral infected state was confirmed by MTT assay. To perform the MTT assay, RAW 264.7 was implanted into a 96 well plate and treated with GFP expressing virus. After 48 hours, 100 μl of 1 mg/ml MTT solution was added reacted to the cells for 4 hours. Then, 150 μl of DMSO was added to dissolve the formazan salt produced in the cells. The amount of this formazan was measured at 540 nm using a microplate reader.

FIG. 1A shows the cell viability of RAW 264.7 against influenza virus (PR8). In the case of Experimental Group where the *Lactobacillus* fermentation drink prepared in Preparation Example 2 of the present invention was diffused, the mouse macrophage line RAW 264.7 showed about 85% cell viability. In Comparative Experimental Group, mouse macrophage cell line RAW 264.7 showed about 70% cell viability.

On the other hand, in Positive Control where only the PR8 virus was inoculated, the macrophage line RAW 264.7 showed about 60% cell viability. Thus, in Experimental Group of the present invention, the survival rate of macrophage cell line RAW 264.7 was increased about 25% compared with that of Positive control inoculated with PR8 virus alone. The viability of macrophage cell line RAW 264.7e, FIG. 1A shows the cell viability of RAW 264.7 against influenza virus (PR8). it was increased by about 10% compared to that of Comparative Experimental Group. It is confirmed that *Lactobacillus* fermented drink of the present invention has as antiviral activity.

The invention claimed is:

1. A process for preparing a health functional food product comprising the steps of:
    preparing a sponge and a dough by adding and mixing 1.0 to 10 wt part of a whey powder as to 100 wt part of a dough; and
    baking the dough for preparing a health functional bakery product after adding, mixing and fermenting 0.01 to 1.0 wt part of a mixture of probiotic preparation consisting of *Leuconostoc* strain, *Lactobacillus* strain and 2 kinds of *Saccharomyces* strains,
    wherein said mixture of probiotic preparation consists of *Leuconostoc* sp. nhs210 strain (accession No.: KCTC-11226BP), *Lactobacillus* sp. nhs221 strain (accession No.: KCTC-11749BP), *Saccharomyces* sp. CCRG321 strain (accession No.: KCTC-13300BP) and *Saccharomyces* sp. nhs321 strain (accession No.: KCTC-11227BP),
    wherein said *Saccharomyces* sp. CCRG321 strain (accession No.: KCTC-13300BP) is isolated and obtained by the steps comprising:
        spreading PDA (Potato dextrose agar) separation medium containing 3 wt % whey powder in the flat plate;
        inoculating and culturing a wild type baker's yeast as parent strain; and
        isolating a fast and optimally growing yeast strain with 3 times subculturing.

* * * * *